(12) United States Patent
Heikkilä et al.

(10) Patent No.: US 6,395,893 B1
(45) Date of Patent: May 28, 2002

(54) CRYSTALLIZATION OF LACTITOL, CRYSTALLINE LACTITOL PRODUCT AND USE THEREOF

(75) Inventors: Heikki Heikkilä, Espoo; Johanna Nygren, Virkkala; Marja-Leena Sarkki; Håkan Gros, both of Kantvik; Olli-Pekka Eroma, Kotka, all of (FI); Julita Pearson, Kent; Tammy Pepper, Surrey, both of (GB)

(73) Assignee: Xyrofin Oy, Kotka (FI)

( * ) Notice: Subject to any disclaimer, the term of this patent is extended or adjusted under 35 U.S.C. 154(b) by 0 days.

(21) Appl. No.: 09/646,411

(22) PCT Filed: Mar. 17, 1999

(86) PCT No.: PCT/FI99/00206
§ 371 (c)(1),
(2), (4) Date: Nov. 9, 2000

(87) PCT Pub. No.: WO99/47532
PCT Pub. Date: Sep. 23, 1999

(51) Int. Cl.$^7$ ............................. C07H 15/04; A23G 3/00
(52) U.S. Cl. ......................... 536/120; 536/4.1; 536/1.1; 536/127; 426/660
(58) Field of Search ........................ 536/120, 4.1, 1.1, 536/127; 426/660

(56) References Cited

U.S. PATENT DOCUMENTS 5,629,042 A * 5/1997 Serpelloni et al. .......... 426/660
5,726,303 A * 3/1998 Wijnman et al. ........... 536/120

FOREIGN PATENT DOCUMENTS

| DE | 3732141 A1 | * 4/1989 |
| DE | 19615418 | 4/1996 |
| DK | 133603 | 6/1976 |
| EP | 0039981 A1 | 11/1981 |

(List continued on next page.)

OTHER PUBLICATIONS

Wolfrom et al., "Crystalline Lactosito" *J. Am., Chem. Soc.*, 60, (1938) pp. 571–573.

van Velthuijsen, J.A., "Food Additives Derived from Lactose: lactitol and Lactitol Palmitate", *J. Agric. Food Chem.*, 27, (1979) pp. 680–686.

Kivikoski et al., "Crystal Structure of Lactitol", *Carbohydrate Research*, 233 (1992) pp. 189–195.

Halttunen, H., et al., "Influence of Drying to the Structure of Lactitol Monohydrate", *Journal of Thermal Analysis*, 49, (1997) 809–816.

Yajima, K., et al., "Transformation of Lactitol Crystals and Dehydration with Grinding", *Chem. Pharm. Bull.*, 45(10), (1997) 1677–1682.

*Primary Examiner*—Ralph Gitomer
*Assistant Examiner*—Devesh Khare
(74) *Attorney, Agent, or Firm*—Scully, Scott, Murphy & Presser (57) ABSTRACT

The present invention relates to a novel process for the crystallization of lactitol, to a particulate crystalline lactitol product having novel properties, to the use thereof as in foodstuffs, pharmaceuticals and oral hygiene products, as well as to special lactitol sweeteners. The process comprises: contacting a liquid containing dissolved lactitol with gas suspended fine solid particles containing microcrystalline lactitol; causing substantial removal of the solvent component of said liquid and allowing the resulting lactitol material to form an essentially solid composition of matter comprising a multitude of microcrystals of lactitol; and causing said lactitol composition to be conditioned during a further step to provide a product consisting essentially throughtout its entire structure of a multitude of microcrystals of lactitol agglomerated together in a random manner. The invention provides a crystalline lactitol product consisting essentially throughout its entire structure of a multitude of microcrystals of lactitol agglomerated together in a random manner.

50 Claims, 2 Drawing Sheets

FOREIGN PATENT DOCUMENTS

| | | |
|---|---|---|
| EP | 0039981 B1 | 8/1983 |
| EP | 0231643 A1 | 8/1987 |
| EP | 0231643 B1 | 6/1990 |
| EP | 0381483 A1 | 8/1990 |
| EP | 0381483 B1 | 6/1994 |
| EP | 381 483 B1 * | 6/1994 |
| EP | 0456636 B1 | 3/1996 |
| EP | 0832899 A1 | 4/1998 |
| FI | 942267 | 11/1994 |
| JP | 19674/90 | 8/1990 |
| JP | 2196794 | 8/1990 |
| JP | 2255694 | 10/1990 |
| WO | WO 90/06317 | 6/1990 |
| WO | WO-90/06317 * | 6/1990 |
| WO | WO 92/16542 | 10/1992 |
| WO | WO-92/16542 * | 10/1992 |
| WO | WO 97/39739 | 10/1997 |
| WO | WO 98/11878 | 3/1998 |

* cited by examiner

CRYSTALLIZATION OF LACTITOL, CRYSTALLINE LACTITOL PRODUCT AND USE THEREOF

The present invention relates to a novel process for the crystallization of lactitol, to a particulate crystalline lactitol product having novel properties, to the use thereof as in foodstuffs, pharmaceuticals and oral hygiene products, and to a special sweetener. The present invention specifically provides a crystalline lactitol product, wherein the crystals are produced by microcrystallization of lactitol from a liquid solution of lactitol.

Lactitol is a sweetener which can be used as a total or partial replacement for sucrose, however, its energy content is only about half of that of sucrose, and it does not cause increased blood glucose content; furthermore, it is non-cariogenic and hence tooth-friendly. Lactitol also can be used as an active ingredient and an excipient in pharmaceutical preparations, e.g. as a laxative.

The preparation of lactitol from lactose has been known for a long time. Industrially, lactitol is prepared from lactose by hydrogenation in the presence of a Raney nickel catalyst. The preparation is described e.g. in Wolfrom, M. L., et al., J. Am. Chem. Soc. 60, (1938) p. 571–573.

Crystalline lactitol is reported to occur in the anhydrous form as well as in the form of a monohydrate and dihydrate. Lactitol also crystallizes as a trihydrate. There seem to exist more than one distinct crystalline form of anhydrous lactitol.

Crystalline lactitol monohydrate as well as the di- and trihydrate and anhydrous lactitol may be used as sweetening agents resembling sugar. For instance, crystalline lactitol monohydrate may be used in dietetic products, confectionery, bakery products, cereals, desserts, jams, beverages, chocolate, chewing gums and ice-cream. The lactitol crystals may also be used in the production of oral hygiene products such as tooth pastes, and in the manufacture of pharmaceuticals.

Anhydrous lactitol may be crystallized from an aqueous solution as described in WO 92/16542. incorporated herein by reference. Anhydrous lactitol has a melting range of 149–152° C.

Lactitol hydrate powders dehydrated to a moisture content of less than 3% have been prepared by drying both lactitol solution and crystalline hydrate. The hygroscopicity of these powders is utilized in drying moist mixtures (European Patent Application 0231643).

Crystallization of lactitol from aqueous solutions and the crystal structures of lactitol have been reported, among others, in van Velthuijsen, J. A., J. Agric. Food Chem. 27, (1979) p. 680; European Patent 0 039 981; J. Kivikoski et al. Carbohydrate Research, 233 (1992) 53–59; EP Patent Application 0 381 483; EP Patent 0456636; JP Patent Application 13220/89. The disclosures of said publications are incorporated herein by reference.

The crystallization of lactitol from a liquid such as from an aqueous or ethanolic solution requires specific crystallization conditions and fairly long crystallization times. Due to the nature of prior art suspension crystallization methods, all of the lactitol in the solution generally cannot be obtained in crystalline form. A part of the lactitol will always remain in the mother liquor and will be discarded with the mother liquor even after repeated series of crystallizations.

Lactitol can also be produced in solid form by granulation as described in background art PCT/FI97/00548. Spray drying of lactitol has also been attempted according to JP open-laid Patent Hei 2-255694 but the tests made were accompanied by many problems. Co-spray drying of a polyol composition containing mainly mannitol and up to 10% lactitol is described in WO 97/39739.

Thus, there exists a need for improving the production of solid lactitol and the present invention aims at satisfying that need.

The object of the present invention is thus, to provide a solid particulate crystalline lactitol product.

Another object of the present invention is to provide crystalline lactiol in a process which transforms a lactitol liquid into a solid lactitol product in one single overall operation.

An object of the invention is also to provide a novel particulate lactitol product which is suitable for use in the food industry as well as in the pharmaceutical and oral hygiene product industry.

A further object of the present invention is to provide a directly compressible lactitol product.

An object is also to provide novel edible, pharmaceutical and oral hygiene products containing lactitol.

Consequently, the present invention, as defined in the appended claims, provides a novel process for producing crystalline lactitol. Said process comprises contacting a liquid containing dissolved lactitol with gas suspended solid particles containing solid lactitol; causing substantial removal of the solvent component of said liquid and allowing the resulting lactitol material to form a composition of matter comprising a multitude of microcrystals of lactitol; and causing said lactitol composition to be conditioned during a further drying step to provide a product consisting essentially throughout its entire structure of a multitude of microcrystals of lactitol agglomerated together in a random manner.

In a preferred embodiment of the invention an aqueous solution of lactitol is got into contact with fluidized particles of microcrystalline lactitol, the wetted particles are dried in a flow of warm gas, and the lactitol on the surface of the particles is allowed to form new microcrystals.

By further conditioning the particles, the microcrystallization is allowed to proceed for a sufficient time to provide a final product consisting essentially of microcrystalline lactitol.

In a preferred embodiment of the invention the wetted particles are substantially dried while falling down with a co-current air stream and allowed to settle into a porous layer of agglomerated microcrystallizing lactitol, which is then conditioned and cooled. The microcrystallization conditions are selected so that the cooled layer is porous and brittle. If desired, the layer may be broken up into smaller fractions. Only a mild crushing action is needed to break up the agglomerated mass of microcrystals. The agglomerated product will primarily be broken up at the interfaces between individual crystals rather than by disrupting the crystals themselves.

In another embodiment of the invention the particles are retained in a gas suspended state in an air stream while additional liquid is sprayed onto their surfaces until the particles have grown to a predetermined size or weight. The particles are then removed from the air stream, e.g. by gravity and conditioned as described above.

The gas suspended microcrystalline lactitol particles are preferably provided by recirculating a portion of the microcrystalline lactitol produced in the process itself. Said particles may comprise dust entrained in circulating drying air or it may be dust or fine particles provided by the crushing of the agglomerated mass. At start-up milled crystalline lactitol may be used as solid feed to be replaced by microcrystalline lactitol when available.

The terms "microcrystalline" and "microcrystal" as used throughout the present specification and claims should be understood to mean very small crystals having a size which on an average is below 50µ, and generally is of the order of about 5–10µ, on an average. In contrast to the present microcrystals, the lactitol crystals obtainable by prior known crystallization techniques are discrete crystals which, on an average, are of the order of about 100–1000µ or larger.

Consequently, the present invention provides a novel particulate crystalline lactitol product wherein each particle substantially throughout its entire structure consists of a multitude of microcrystals of lactitol agglomerated together in a random manner.

Although the size of the lactitol particles according to the present invention is not critical and may vary according to the intended use of the product, the mean particle size of the lactitol product is generally below 10 mm, typically between about 0.1 and 2.0 mm. The preferred mean particle size is generally about 0.15–0.4 mm. The particle size and distribution may be control-led to sure intended use.

The microcrystals may be used as said discrete particles, they may be compressed and tabletted or they may even be given the form of ordinary sugar lumps or cubes.

The individual lactitol microcrystals generally comprise anhydrous lactitol and/or lactitol monohydrate. The crystal mass may also include other lactitol hydrate forms, such as lactitol dihydrate and/or amorphous lactitol. It is, however, for many applications preferred that the major crystalline form is anhydrous or monohydrate. In a preferred embodiment of the invention, the microcrystals consist essentially of anhydrous lactitol.

The microcrystalline lactitol product according to the present invention may be used as a bulk sweetener for the total or partial replacement of sucrose or other sweetening agents. Thus, it is useful in dietetic products, confectionery, bakery products, cereals, desserts, jams, beverages, chocolate, chewing gums and ice creams. It is also useful in pharmaceuticals such as laxatives and in oral hygiene products such as tooth pastes.

The microcrystalline lactitol product according to the present invention is particularly useful for tabletting purposes due to its agglomerated crystal structure, and partly also because of the presence of different physical forms of particles. The product may, for instance, be used as a tabletting excipient in the same way as lactose.

A further embodiment of the present invention relates to a special sweetener which comprises microcrystalline lactitol. Such a sweetener may include other components such as excipients and/or other sweeteners.

Such other sweeteners are preferably also non-cariogenic sweeteners such as intense sweeteners taken from the group comprising dipeptide sweeteners, saccharin, acesulfame K, stevioside, cyclamate, sucralose and neohesperidin dihydrochalcone. However, the preferred non-cariogenic sweetener consists essentially of the microcrystalline lactitol according to the invention.

The excipients which may be used in the sweetener and/or other applications such as in pharmaceutical preparations may comprise, for instance, microcrystalline cellulose, carboxymethyl cellulose, polydextrose, dextrose, maltodextrin, lactose, sugar, etc. as well as other sugar alcohols. The microcrystalline lactitol according to the present invention may also be used in preparations as a substantially inert component such as a diluent, carrier and/or excipient.

The microcrystalline lactitol of the present invention is preferably produced in a pure lactitol form, i.e. containing throughout essentially only lactitol. Although the lactitol may be mixed with other compounds, lactitol should always form the major portion of the composition and preferably the product should contain over 80%, preferably more than 90% and most preferably more than 98% lactitol.

If the solid and/or liquid feed comprises other components, such as one or more of the above mentioned excipients, or other active ingredients, the product discharged from the microcrystallization apparatus will contain said other component(s) as an integral part of its structure. A secondary spray of another solid or liquid component may also be fed into the microcrystallization apparatus into contact with the microcrystallizing lactitol. Said other compounds should be selected so as to not interfere adversely with the microcrystallization of the lactitol.

Further embodiments of the present invention relate to products made from the novel microcrystalline lactitol. Such products are typically edible products, pharmaceutical products and/or oral hygiene products such as those mentioned above. Special advantages are obtained, for instance, in the production of chocolate from the microcrystalline lactitol of the present invention.

A further embodiment of the invention relates to a directly compressible crystalline lactitol product comprising the novel microcrystalline lactitol and to tablets produced by compressing a composition containing such microcrystalline lactitol.

The present invention will now be described in greater detail. This description should, however, not be taken as limiting the invention to the precise wording thereof. A person skilled in the art will be able to provide numerous modifications and variations of the process without deviating from the invention as defined in the appended claims.

BRIEF DESCRIPTION OF THE DRAWINGS

The microcrystalline lactitol produced according to the present invention is shown in the accompanying drawing, wherein.

In the process according to the present invention a liquid containing dissolved lactitol is provided. The solvent component of said liquid is preferably water, although lactitol may also be microcrystallized from other solvents such as alcohols, e.g. isopropanol.

The lactitol concentration of said aqueous solution should be between about 30% by weight and about 80% by weight in order to provide a suitable supersaturation at the crystallization. Said concentration is preferably about 40–70% by weight.

Prior to feeding the liquid into a microcrystallization apparatus, the liquid is preferably warmed in order to facilitate the subsequent removal of the solvent component and in order to more quickly provide suitable crystallization conditions in said apparatus. An aqueous solution is preferably warmed to a temperature of about 45–80° C. preferably about 50–70° C. prior to feeding into said apparatus.

The liquid should preferably be distributed in the form of small droplets in the microcrystallization apparatus. The liquid is preferably fed at a pressure through one or more nozzle(s) into said apparatus. In the apparatus liquid is brought into contact with solid particles containing solid lactitol which are simultaneously fed into the apparatus so as to be fluidized or suspended in said apparatus.

The solid lactitol particles may comprise microcrystalline lactitol particles recirculated from the microcrystallization apparatus. Most preferably a fine fraction of the product is recirculated. Such a fine fraction typically has a mean particle size below about 0.2 mm, preferably below about 0.1 mm. However, when larger individual product particles are desired, correspondingly larger lactitol particles may be recirculated or fed into the apparatus from another source. The solid particles may also be dust or fine particles entrained in the drying air and fed back into the apparatus as solid feed.

The liquid is generally contacted with the suspended solid particles in an upper portion of the microcrystallization apparatus. Here the wetted particles and any free droplets of lactitol solution meet a drying gas such as heated air which is introduced into the apparatus to provide removal of the solvent component of said liquid. The drying air is preferably heated to a temperature of about 60–200 °C., preferably about 90–160° C., most preferably to about 100–130° C. A higher temperature favours the production of anhydrous lactitol, while a lower temperature allows formation of lactitol monohydrate and/or other hydrate forms.

The drying should be accomplished in such a way as to substantially remove the solvent while said lactitol material is still in a suspended state. When the solvent is water, said drying should provide a suspended lactitol material dried to a free moisture content of about 0.1 to 5%, preferably 0.1 to 3%. The free moisture is calculated as any water which is not bound as crystal water in the microcrystallizing lactitol.

In case the drying is not sufficient or too much liquid has been fed into the apparatus, the lactitol material will be too wet and the crystals will stick together to form a dense structure.

The suitable ratio of lactitol liquid to solid lactitol varies with the microcrystallization conditions. The ratio should be selected so as to provide a wetting of the solid particle surfaces without dissolving the core of the seed particles. The amount of solvent component also depends on the ease of volatilization of the solvent and on the temperature of the liquid feed as well as the temperature and amount of the drying gas.

The wetted particles may be dried by a co-current or a counter-current stream of drying air. The co-current air will flow downwards with the falling particles while a counter-current air stream will retain the particles in a suspended state for a longer time.

The particles carried downwards with a co-current air stream in a microcrystallization apparatus should be substantially dry by the time they reach the bottom portion of the apparatus and are allowed to settle there. The settling surface is preferably a means allowing building up of a suitable layer and for adjusting the reaction time in the layer. A belt moving at a speed sufficient to allow build up of a porous agglomerated layer of lactitol is generally sautable. The layer typically has a thickness of about 0.5 to 5 cm, preferably about 1–3 cm.

The agglomerated layer of solidified lactitol should further be conditioned so as to allow microcrystallization to proceed in the layer. Said conditioning preferably includes two or more separate steps or phases with different temperatures. The layer is heated e.g. by blowing a drying gas therethrough. The temperature and amount of the drying gas is selected so as to provide suitable microcrystallization conditions in the layer. A higher temperature will favour the formation of anhydrous lactitol. The temperature of the drying gas is typically about 50–160° C. A conditioning at a temperature of about 50–70° C. will favour production of lactitol monohydrate microcrystals while a conditioning temperature of about 80–130° C. will produce predominantly anhydrous lactitol microcrystals.

The conditioning should continue for a sufficient time to allow microcrystallization of any solubilized lactitol to take place in the layer. Typically, the conditioning should continue for a time of about 10–180 min or more, preferably about 20–40 min.

After conditioning, the agglomerated particle layer is preferably post-conditioned and cooled or is allowed to cool to ambient temperature. If the surface on which the layer is allowed to settle is flat, the result will be a substantially flat porous and brittle plate comprising microcrystalline lactitol. However, the microcrystallizing lactitol may also be gathered in forms or molds having any desired form such as resembling ordinary sugar lumps, or bars, strings, cubes, spades, hearts, flowers, etc.

When the microcrystalline product is in the form of a continuous layer, it is generally desirable to break up the agglomerated layer to provide discrete particles. Only a mild comminuting action is required for breaking up the bonds between individual microcrystals.

The resulting microcrystalline lactitol particles are preferably fractionated after an eventual milling and a portion thereof is recirculated to provide a feed of solid particles containing microcrystalline lactitol into the top portion of the microcrystallization apparatus.

Generally the microcrystalline lactitol particles are broken up so as to provide particles having a mean particle size of about 0.1–10 mm, preferably about 0.15–0.4 mm. It is generally desirable to recirculate fine particles having a mean particle size below about 0.2 mm, preferably below about 0.1 mm, although larger particles may be recirculated, especially in cases where the desired end product comprises larger particles.

In the case where the drying air is blown counter-current to the downward movement of the wetted particles in the microcrystallization apparatus, the particles will be fluidized therein. By a suitable fluidization action the particles will be made to recirculate within the apparatus. In the apparatus a simultaneous wetting, drying and microcrystallization of particles will take place. Each particle will pass through several wetting and drying/microcrystallization stages, colliding with other particles and growing ever bigger until the particle reaches the size and weight wherein the fluidizing air no longer manages to retain them in a fluidized state. At this stage the particles will fall to the bottom of the apparatus and may be removed therefrom to be conditioned, for instance as described above.

The solid feed to the microcrystallization apparatus in the counter-current case preferably comprises dust, and fine particles recovered from the circulation of drying air.

In the particulate microcrystalline lactitol product according to the present invention each particle substantially throughout its entire structure consists of a multitude of microcrystals of lactitol agglomerated together in a random manner. The lactitol purity of the product is preferably more than 80%, preferably more than 90%, most preferably up to 98% or more.

In the preferred particles about 10–90%, preferably about 30–70% of the dry substance derives from a feed of solid microcrystalline particles, preferably recirculated from the production line or from the drying air. The co-current system may require slightly more solid feed than does the counter-current system. Thus, for the co-current driving system. the preferred amount of dry substance deriving from the solid particles is 50–70%.

The microcrystals in each product particle of the present invention are individually very small compared to the crystals formed by prior art crystallization processes. Generally, the size of the microcrystals in each particle is on an average below 50μ, preferably about 5–10μ on an average.

Depending on the production parameters, especially the temperature used during microcrystallization, the lactitol crystallizes predominantly either as monohydrate or anhydrous microcrystals. Higher temperatures favour the production of anhydrous crystals. The particles may comprise pure individual crystalline forms, or they may comprise mixtures of various forms of lactitol crystals. Lactitol hydrate forms containing two or three molecules of bound crystal water may also form initially but the drying conditions are generally selected so as to make these hydrates lose at least some of the bound water. A mixture of lactitol monohydrate and anhydrous lactitol crystals with some amorphous lactitol is generally produced.

The degree of crystallinity of the product is, however, generally high. According to DSC measurements the degree of crystallinity is generally as high as 90% or more.

The water content of the preferred microcrystalline lactitol product varies according to production parameters in the range of 0.1% to about 6%. Thus, the microcrystalline lactitol product according to the invention quite often will have a water content between those of pure anhydrous lactitol and pure lactitol monohydrate.

The melting behaviour generally shows peaks, measured with differential scanning calorimetry (DSC), at least at the melting ranges of lactitol monohydrate (about 95–100° C.) and anhydrous lactitol (about 145–150° C.). However, there are frequently DSC peaks also at the melting range of another anhydrous form (about 120–123° C.) and even at the dihydrate melting range (about 72–78° C.). The actual melting usually takes place at the higher anhydrous lactitol melting range since there is almost always some anhydrous lactitol in the sample. Since the particles contain a myriad of small crystals with mutually different melting behaviours, the product generally cannot be regarded as a pure crystalline form of lactitol.

The invention will now be illustrated with the aid of a few examples. These examples should in no way be taken as limiting the invention.

EXAMPLE 1

A lactitol solution (concentration 49.6% by weight, purity over 99% on D.S.) was fed into a heated feed tank. The temperature of the solution in the feed tank was kept at 52±2° C. Solution was supplied from the tank to a top spray nozzle at a rate of 28 kg/h. The feed pressure of the solution varied from 130 to 150 bar.

Simultaneously with the solution small particles of dried product were fed to the nozzle at a rate of 23 kg/h. Drying air was also fed into the apparatus to dry the sprayed solution and wetted particles. The temperature of the air was adjusted to about 100–105° C. The partly dried droplets and dry feed mixture fell co-currently with the air-stream towards the bottom screen having a temperature of 45–65° C.

The apparatus was operated under these conditions for nine minutes. During this time an agglomerated, porous powder layer having a thickness of about 2 cm built up on the screen. The lactitol layer was conditioned on the screen for about 30 minutes and the temperature dropped slowly from 50° C. to 45° C. The microcrystallized product was collected from the screen, subjected to a gentle milling and sieved.

The water content of the microcrystalline lactitol product was found to be 3.5%.

EXAMPLE 2

The procedure of Example 1 was repeated several times under varying test conditions. The solid feed comprised recirculated microcrystalline lactitol. The test conditions are indicated in Table 1.

The water content of the microcrystalline lactitol product was analyzed by the Karl Fischer method and the melting behaviour was measured by differential scanning calorimetry (DSC).

The analysis results of the products are shown in Table 2.

TABLE 1

Lactitol microcrystallization conditions

| Test | Time min | Feed pressure bar | Feed soln. Conc. D.S. % | temp. ° C. | Drying air temp. ° C. | Temp. under screen ° C. | Temp. above screen ° C. | Feed dry kg | End prod. kg | DS fr. soln. % |
|---|---|---|---|---|---|---|---|---|---|---|
| 1 | 0 | 30 | 51.1 | 50–54 | 100 | 64 | 64 | 2.5 | | |
|   | 15 | 40 |   |   | 112 | 54 | 52 |   | 7.0 | 64 |
| 2 | 0 | 60 | 51.1 | 50–54 | 108 | 65 | 64 | 3.3 | | |
|   | 6 | 45 |   |   | 119 | 58 | 58 |   | 4.1 | 20 |
| 3 | 0 | 30 | 51.1 | 50–54 | 104 | 70 | 72 | 2.8 | | |
|   | 6 | 50 |   |   | 108 | 57 | 57 |   | 4.0 | 30 |
| 4 | 0 | 75 | 49.6 | 50–54 | 100 | 71 | 69 | 4 | | |
|   | 16 | 80 |   |   | 100 | 50 | 50 |   | 6.6 | 39 |
| 5 | 0 | 40 | 49.6 | 50–54 | 96 | 58 | 61 | 3 | | |
|   | 19 | 70 |   |   | 109 | 52 | 55 |   | 5.5 | 45 |
| 6 | 3 | 90 | 49.6 | 50–54 | 99 | 53 | 55 | 3 | | |
|   | 8 | 110 |   |   | 102 | 45 | 48 |   | 4.3 | 30 |
| 7 | 0 | 80 | 49.6 | 50–54 | 96 | 58 | 61 | 1.9 | | |
|   | 4 | 80 |   |   | 104 | 49 | 50 |   | 2.8 | 32 |
| 8 | 0 | 100 | 49.6 | 50–54 | 126 | 74 | 82 | 3.6 | | |
|   | 9 | 130 |   |   | 98 | 45 | 47 |   | 5.9 | 39 |
| 9 | 0 | 140 | 49.6 | 50–54 | 100 | 57 | 65 | 3.5 | | |
|   | 9 | 130 |   |   | 104 | 44 | 47 |   | 5.6 | 38 |

TABLE 1-continued

Lactitol microcrystallization conditions

| Test | Time min | Feed pressure bar | Feed soln. Conc. D.S. % | temp. °C. | Drying air temp. °C. | Temp. under screen °C. | Temp. above screen °C. | Feed dry kg | End prod. kg | DS fr. soln. % |
|---|---|---|---|---|---|---|---|---|---|---|
| 10 | 0 | 50 | 54.2 | 64–67 | 81 | 57 | 57 | 4.4 | | |
|    | 8 | 60 | | | 100 | 48 | 52 | | 5.6 | 22 |
| 11 | 0 | 70 | 54.2 | 64–67 | 80 | 59 | 57 | 4.9 | | |
|    | 10 | 110 | | | 99 | 52 | 54 | | 8.4 | 42 |

TABLE 2

Water contents of the product

| Test | Water % | Description | DSC peaks at °C. | °C. | °C. |
|---|---|---|---|---|---|
| 1 | 4,5 | Good layer | 86,4 | 150,6 | |
| 2 | 0,6 | Good layer | 96,1 | 122 | 152,5 |
| 3 | 2,6 | Good layer | 93,8 | 152,3 | |
| 4 | 3,9 | Good layer | 94,5 | 152 | |
| 5 | 5,3 | Good layer | 93,9 | 142,9 | |
| 6 | 3,8 | Good layer | 94,3 | 152,5 | |
| 7 | 2,4 | Good layer | 76,8 | 92,4 | 152,9 |
| 8 | 5,1 | Good layer | 93,9 | 146,5 | |
| 9 | 3,5 | Good layer | 78,4 | 93,3 | 153,4 |
| 10 | 5,0 | Good layer | 96,7 | 134,1 | 145,3 |
| 11 | 5,4 | Good layer | 97 | 146,8 | |

The degree of crystallinity was measured for runs No. 10 and 11 by DSC and was found to be 94 to 95%.

EXAMPLE 3

A continuous fluid bed microcrystallization is performed in an apparatus having a fluid bed drying chamber, equipped with a spray nozzle system inside in the middle of the chamber. The apparatus comprises a bottom screen with a hole for the discharge of the heaviest particles, and a cyclone to recover light particles.

The chamber is loaded with 1 kg of powdered lactitol to act as seed material for the microcrystallization of lactitol. The powdered lactitol is fluidized with a flow of air (temperature 100–105° C.) through the bottom screen. A lactitol solution (concentration 50%, purity over 99% D.S.) at a temperature of 50° C. is fed into the chamber with a pump, atomized by means of a nozzle and sprayed over the fluidized lactitol powder.

The solution is supplied at a rate of 1 kg/h to the fluidized lactitol powder. The air flow rate is adjusted to fluidize the lactitol and to evaporate water at a rate sufficient to crystallizes the lactitol. A microcrystalline lactitol agglomerate is formed when lactitol crystallizes around the lactitol powder particles. The agglomerates remain in a fluidized state until they fall down when their weight is high enough. Lactitol agglomerates are discharged continuously through the bottom hole.

In the drying chamber the lightest, non-agglomerated lactitol particles are removed from the top of the chamber entrained in the exiting air stream. This fine lactitol material is recovered in a cyclone and fed back to the chamber to act as a continuous seed stream.

The discharged agglomerated product is conditioned at a temperature of 45–50° C. for 30 minutes to balance the microcrystallization.

Steady state conditions are reached when all the powdered lactitol used as a starting seed has been discharged from the process. The product obtained thereafter is a totally microcrystalline product which throughout its entire structure consists of microcrystalline lactitol.

EXAMPLE 4

A microcrystalline lactitol product having a water content of about 5% was assessed in a standard chocolate production.

The following ingredients were used

| | |
|---|---|
| Cocoa Liquor (BCM) | 13.4% |
| Full Cream Milk Powder (Kerrygold Ingredients) | 13.4% |
| Microcrystalline lactitol | 44.0% |
| Litesse II (Cultor Food Science Inc.) | 4.8% |
| Cocoa Butter (BCM) | 23.7% |
| Vanillin (Claremont Ingredients) | 0.2% |
| Lecithin | 0.5% |

The milk powder, microcrystalline lactitol, Litesse II (modified polydextrose), vanillin and cocoa liquor were mixed in a Stephan mixer with a portion of the cocoa butter. The mixture was passed through a three roll refiner to produce a flake. The flake was mixed again in the Stephan mixer and a farther portion of cocoa butter was added. The mix was re-refined with the pressures increased to produce a flake with an acceptable particle size.

The resulting flakes were stored ready for conching. Prior to conching the flakes were pre-warmed in an oven set to 50° C. The flake was added to a conche with the temperature set to 60° C. On loading the remaining cocoa butter was added to give a final fat content of 35 %. A small amount of the lecithin was added at this stage. The sample was conched for 24 hours. The remaining lecithin was added I hour prior to the removal of the batch from the conche.

For the sake of comparison the procedure was repeated identically with another batch except that the microcrystalline lactitol was replaced by standard crystalline lactitol monohydrate (Lactitol MC, Xyrofin Oy).

During the production of the two batches there were no significant processing differences. Neither batch showed any difficulties and the resulting chocolates were both acceptable.

A particle size analysis of the two batches showed that an acceptable particle size was achieved in both cases. There was an insignificant increase in the particle size of the chocolate made using microcrystalline lactitol (10–12 $\mu$m) compared to the one with lactitol monohydrate (9–10 $\mu$m).

The viscosity of the two samples was measured using a Haake RV20 viscometer with an RC20 rheocontroller fitted. It was found that the viscosity of the sample made with the microcrystalline lactitol according to the present invention showed no significant increase in viscosity when held at 50° C. for one week, while the sample with lactitol monohydrate showed considerable thickening when stored at 50° C. The absence of thickening in the chocolate made with the microcrystalline lactitol is a distinct advantage over lactitol monohydrate and completely unexpected for a sweetener containing about 5% moisture, either free or bound.

EXAMPLE 5

A set of standard recipe madeira cakes were produced using microcrystalline lactitol according to the present invention, commercial crystalline lactitol (Xyrofin Oy) and milled lactitol (Xyrofin Oy).

The lactitols were respectively mixed with sorbitol, flour, high ratio fat, skimmed milk powder, egg, salt, baking, powder, spray dried egg powder and acesulfame K. The mix was deposited in paper cases and cooked in the oven at 210° C. for 30–35 minutes.

The cakes produced with the microcrystalline lactitol were equally good in quality as the two other batches.

EXAMPLE 6

A sample of microcrystalline lactitol produced according to the present invention was assessed in tablet production and compared to standard lactitol monohydrate (Lactitol MC, Xyrofin Oy) and a granulated lactitol product produced according to the teaching of the above mentioned Patent Application PCT/FI97/00548 (Finlac DC, Xyrofin).

The material under evaluation was mixed in a laboratory scale Turbula mixer for 2 minutes with 0.5% magnesium stearate as lubricant. The mixed sample was then tabletted on a Manesty 2C single punch press using a 15 mm diameter flat-faced bevelled edge punch.

The compression force was adjusted by altering the drop of the top punch. The compression force is indicated by an arbitrary figure. The higher the number, the greater the compression. These figures can only be used as a comparison for each series of compressions. As soon as the material is changed or any of the machine settings are altered the numbers cannot be compared. The adjustment is such that it cannot be exactly reproduced, therefore, these figures should only be seen as a means of differentiating between samples and indicating either increasing or decreasing compression force.

Tablet hardness was measured using a Key Instruments tablet hardness tester which measures the force required to break the tablet across its diameter. Ten tablets were tested and an average reading recorded.

The thickness of ten tablets was measured using a micrometer gauge. The average of ten tablets is recorded.

Ten tablets were weighed individually and an average recorded.

Tablet friability was measured using a Key Instruments friability tester. Ten tablets were dropped 100 times and the percentage weight loss recorded. Any tablets that are badly chipped are removed prior to weighing.

The results obtained from tabletting microcrystalline lactitol are tabulated in Table 3. This material tabletted well producing acceptable tablets over a range of compression forces. The maximum hardness achieved was over 300 N. The friability of these tablets was acceptable for all the tablets produced with hardness result >100N.

The results obtained from tabletting crystalline lactitol monohydrate are tabulated in Table 4. This material did not tablet well producing poor compacts with a maximum hardness of <70N. In all cases the tablets were poorly formed giving unacceptable friability results, with all of the tablets totally disintegrating during the test.

The results obtained from tabletting granulated lactitol are tabulated in Table 5. This material produced good tablets over a range of compression forces. Hardness results obtained for these samples were not as high as those seen for the microcrystalline lactitol samples, with a maximum of 240N compared to >300N. The friability of the tablets produced with microcrystalline lactitol was still better than that of the tablets produced with granulated lactitol.

TABLE 3

Microcrystalline Lactitol Sample

| Compression* | 34.5 | 34 | 33.5 | 33 | 32.5 | 32 |
|---|---|---|---|---|---|---|
| Weight (g) | 0.981 | 0.994 | 0.979 | 0.981 | 0.995 | 0.998 |
| Thickness (mm) | 3.859 | 3.9 | 3.864 | 3.95 | 4.18 | 4.4 |
| Hardness (N) | 330 (344) | 134 (335) | 319 (301) | 252(257) | 156(137) | 90(85) |
| Friability (10 tabs) | 0.69 | 0.38 | 0.5 | 0.22 | 0.32 | 1.31 |

TABLE 4

Crystalline Lactitol Monohydrate

| Compression* | 32.5 | 32 | 31.5 | 31 |
|---|---|---|---|---|
| Weight (g) | 1.003 | 1.006 | 1.006 | 0.999 |
| Thickness (mm) | 4.019 | 4.055 | 4.046 | 4.52 |
| Hardness (N) | 61(59) | 62(61) | 67(64) | 68(64) |
| Friability (10 tabs) | 100 | 100 | 100 | 100 |

TABLE 5

Granulated Lactitol

| Compression* | 34 | 33.5 | 33 | 32.5 |
|---|---|---|---|---|
| Weight (g) | 1.007 | 0.989 | 1.018 | 0.99 |
| Thickness (mm) | 4.029 | 4.138 | 4.414 | 4.614 |
| Hardness (N) | 240(307) | 193(213) | 139(133) | 70(82) |
| Friability (10 tabs) | 0.34 | 1.08 | 1.79 | 4.7 |

Figures shown in brackets in Tables 3, 4 and 5 are those taken from analysis performed during production. All other results are from analysis performed ~24 hours after production.

While the standard crystalline lactitol monohydrate produced poor tablets, the microcrystalline lactitol sample according to the present invention showed an improvement even when compared to the granulated lactitol. Tablets that were produced had a higher hardness and produced acceptable tablets over a greater range of compression forces. The friability of these samples was also an improvement on the results seen for the granulated lactitol sample.

EXAMPLE 7

A batch of microcrystalline lactitol produced in accordance with the procedure described in Example 1 was analyzed as to its physical properties. The following analysis methods were used:

Moisture was measured using coulometric Karl Fischer titration

DSC analysis was made at a speed of 10° C./minute

Flowability: A 500 g sample was poured to a 500 ml measuring cylinder. The sample was tapped 10 times, levelled and the amount of the sample was weighed.

Hygroscopicity: 10 g of the sample was weighed to a petri dish. The open dish was put into a humidity cabinet. The change in weight was measured. The humidity cabins at 25° C. and relative humidity 60% and at 40° C. and relative humidity 70% were used.

Particle size distribution: Sieve analysis was used to determine the particle size.

Rate of solution: 100 g of the sample was put in 100 g of water at 20° C. and 40° C. A small paddle mixer, 250 rpm, was used to mix the solution. During the dissolution the refractive index was measured.

Heat of solution: 40 g of the sample was dissolved in 670 g of distilled water at 25° C. The heat of solution was measured with a calorimeter operating in a constant temperature environment.

SEM photos were taken of the microcrystalline lactitol.

The microcrystalline lactitol was compared to a commercial grade lactitol monohydrate (Lactitol MC L125 lot 22117, Xyrofin Oy, Kotka, Finland). The analysis results are indicated in Table 3

TABLE 3

| Analysis | Microcryst. | Monohydr. |
| --- | --- | --- |
| Moisture, % | 5.1 | 5.1 |
| DSC, 10° C./min, peak at | 96.5 | 104.1 |
|  | 147.4 |  |
| Flowability, s | 17 | 23 |
| Bulk density, g/500 ml | 325 | 360 |
| Heat of solution, cal/g | 15.4 | 15.6 |
| Sieve analysis |  |  |
| >0.710 mm | 0.6 | 15.2 |
| >0.560 mm | 2.3 | 17.9 |
| >0.450 mm | 8.3 | 20.6 |
| >0.315 mm | 31.5 | 25.8 |
| >0.250 mm | 21.6 | 15.1 |
| >0.180 mm | 21.1 | 4.8 |
| >0.100 mm | 13.0 | 0.7 |
| 0 | 1.6 | 0.0 |
| Mean particle size, mm | 0.29 | 0.47 |
| Coefficient of variation | 39 | 30 |

Both lactitols contained 5.1% of water. The DSC diagram of the microcrystalline lactitol contained two peaks, while the monohydrate had only one. The microcrystalline lactitol had a better flowability and the bulk density was low. The mean particle size was lower for the microcrystalline lactitol.

100 g of microcrystalline lactitol dissolved in 4 minutes. in 100 g of water at 20° C. compared to about 5 minutes for the monohydrate. The smaller particle size of the microcrystalline lactitol may be one reason for the quicker dissolution rate.

Microcrystalline lactitol absorbed water similarly to lactitol monohydrate in both climate cabins. At 25° C. and 60% relative humidity the water sorption of microcrystalline lactitol was 0.05% compared to 0.02% for the monohydrate. At 40° C. and 70% relative humidity the figures were 0.11% and 0.04%, respectively.

Figure 1:
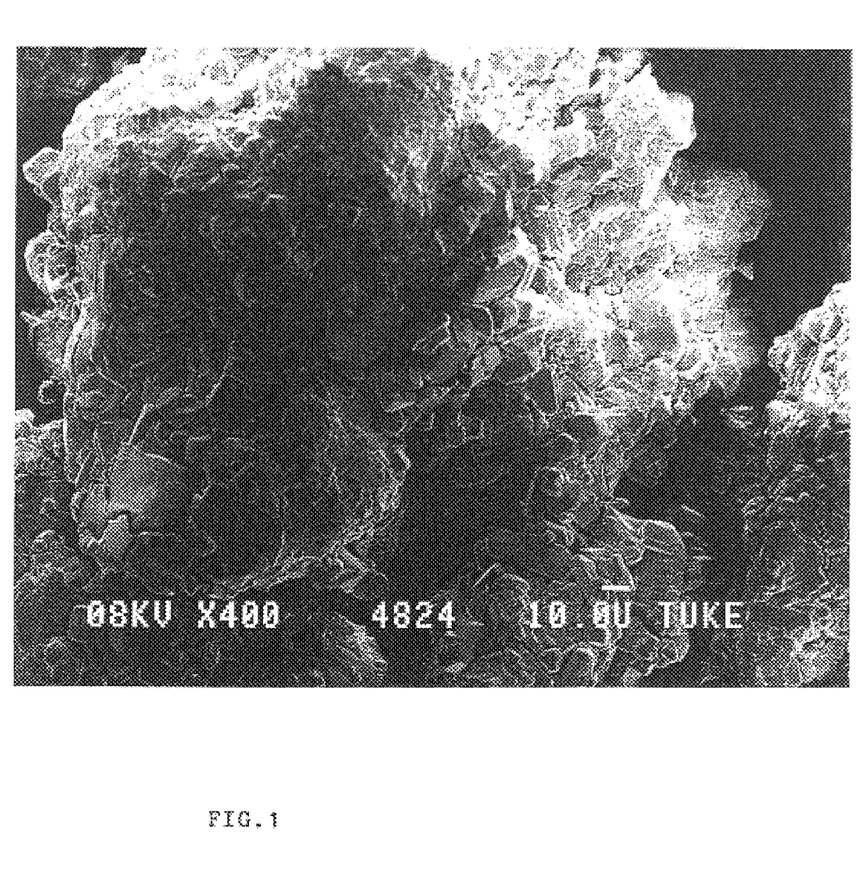
FIG. 1 is a SEM photo showing the microcrystalline structure in 400× magnification.
Figure 2:
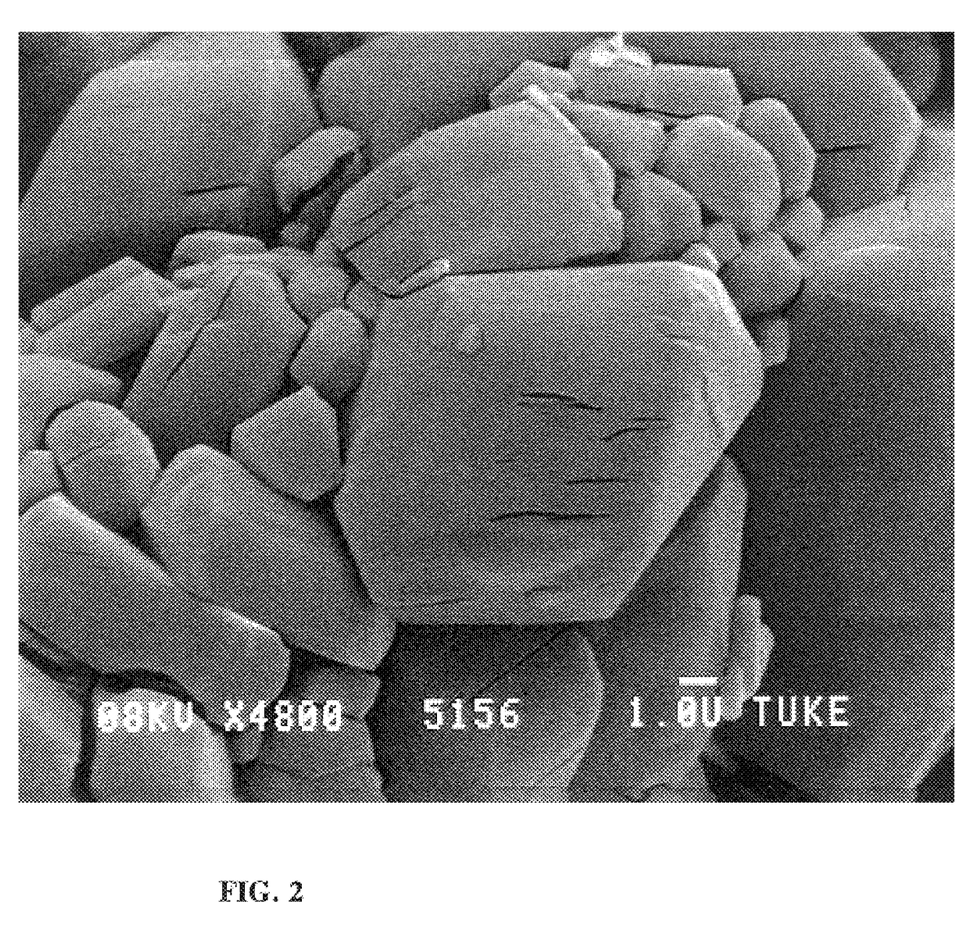
FIG. 2 is a SEM photo showing the microcrystalline structure in 4800× magnification.

The microcrystalline lactitol in SEM photos in 400× magnification (FIG. 1) looked like crystal size lumps which contain small crystals. The microcrystalline structure shows very clearly in 4800× magnification (FIG. 2).

What is claimed is:

1. A process for the crystallization of lactitol, comprising contacting a liquid containing dissolved lactitol with gas—suspended fine solid particles containing microcrystalline lactitol;

causing substantial removal of the solvent component of said liquid and allowing the resulting lactitol material to form an essentially solid composition of matter comprising a multitude of microcrystals of lactitol; and conditioning said lactitol composition to provide a product comprising a multitude of microcrystals of lactitol agglomerated together in a random manner.

2. The process according to claim 1, wherein said liquid is an aqueous solution of lactitol having a lactitol concentration of about 30–80% by weight.

3. The process according to claim 2, wherein said liquid is an aqueous solution of lactitol having a lactitol concentration of about 40–70% by weight.

4. The process according to claim 1, comprising warming said liquid to a temperature of about 45–80° C. prior to said contacting.

5. The process according to claim 4, comprising warming said liquid to a temperature of about 50–70° C. prior to said contacting.

6. The process according to claim 1, wherein said contacting comprises spraying said liquid into contact with said suspended fine solid particles.

7. The process according to claim 1, wherein said liquid contains a minor portion of an excipient, an active ingredient or other sweetener than lactitol.

8. The process according to claim 7, wherein a secondary spray of another liquid containing an excipient, an active ingredient or other sweetener than lactitol is simultaneously provided.

9. The process according to claim 1, wherein said removal of said solvent is performed by the introduction of a drying gas such as air heated to a temperature of about 60–200° C.

10. The process according to claim 9, wherein said solvent is water and said solvent removal provides a lactitol material dried to a free moisture content of about 0.1 to 5%, while said lactitol material is still in a suspended state.

11. The process according to claim 10, wherein said solvent and said solvent removal provides a lactitol material dried to a free moisture content of about 0.1–3%, while said lactitol is still in a suspended state.

12. The process according to claim 9, wherein said removal of said solvent is performed by the introduction of a drying gas such as air heated to a temperature of about 90–160° C.

13. The process according to claim 1, wherein said conditioning comprises drying said lactitol composition.

14. The process according claim 1, wherein said conditioning is maintained to allow lactitol microcrystallization to proceed in said composition.

15. The process according to claim 1, wherein said lactitol composition is allowed to settle on a moving belt and to form thereon a substantially continuous agglomerated porous powder layer having a thickness of about 0.5–5 cm.

16. The process according to claim 15, wherein said conditioning includes treating said composition in said agglomerated layer with a drying gas having a temperature of about 50–70° C., for a time of about 10–180 min or more, to provide a product comprising a major portion of lactitol monohydrate.

17. The process according to claim 16, which further comprises cooling said conditioned agglomerated layer to provide a substantially flat porous and brittle plate comprising microcrystalline lactitol.

18. The process according to claim 17, comprising subjecting said plate to a mild comminuting action so as to break up said agglomerated layer.

19. The process according to claim 15, wherein said conditioning includes treating said composition in said agglomerated layer with a drying gas having a temperature of about 70–100° C. or more for a time of about 10–180 min or more to provide a product comprising a major portion of anhydrous lactitol.

20. The process according to claim 15, wherein said lactitol composition is allowed to settle on a moving belt and to form thereon a substantially continuous agglomerated porous powder layer having a thickness of about 1–3 cm.

21. The process according claim 1, which further comprises fractionating microcrystalline lactitol particles and recirculating at least a portion thereof to provide a feed of said fine solid particles containing microcrystalline lactitol.

22. The process according to claim 21, comprising recovering microcrystalline lactitol particles having a mean particle size of about 0.1–2 mm.

23. The process according to claim 22, comprising recovering microcrystalline lactitol particles having a mean particle size of about 0.15–0.4 mm.

24. The process according to claim 1, wherein about 10–90% of the dry substance derives from a feed of solid microcrystalline particles.

25. The process according to claim 24, wherein about 30–70% of the dried substance derives from a feed of solid microcrystalline particles.

26. The process according to claim 1, comprising recirculating microcrystalline lactitol particles having a mean particle size below about 0.2 mm.

27. The process according to claim 26, comprising recirculating microcrystalline lactitol particles having a mean particle size below about 0.1 mm.

28. The lactitol product according to claim 27, having a lactitol purity of more than 98%.

29. A particulate crystalline lactitol product wherein each particle substantially throughout its entire structure consists of a multitude of microcrystals of lactitol agglomerated together in a random manner.

30. The lactitol product according to claim 29, having a lactitol purity of more than 80%.

31. The lactitol process according to claim 30, having a lactitol purity of more than 90%.

32. The lactitol product according to claim 29, said particles having been produced by microcrystallization of a liquid containing dissolved lactitol together with fine solid particles containing microcrystalline lactitol.

33. The lactitol product according to claim 29, wherein about 10–90% of the dry substance of the final product derives from a feed of solid microcrystalline particles.

34. The lactitol product according to claim 29, comprising particles having a mean particle size of about 0.1–2.0 mm.

35. The lactitol product according to claim 34, comprising particles having a mean particle size of about 0.15–0.4 mm.

36. The lactitol product according to claim 33, wherein about 30–70% of the dried substance of the final product derives from a feed of solid microcrystalline particles.

37. The lactitol product according to claim 29, wherein the size of the microcrystals in each particle is on an average below 50μ.

38. The lactitol product according to claim 37, wherein the size of the microcrystals in each particle is about 5–10 μm.

39. The lactitol product according claim 29, comprising a porous and brittle composition containing microcrystals of anhydrous lactitol and lactitol monohydrate.

40. The lactitol product according claim 29, wherein said microcrystals substantially comprise lactitol monohydrate.

41. The lactitol product according to claim 29, wherein said microcrystals substantially comprise anhydrous lactitol.

42. The lactitol product according to claim 29, wherein the microcrystals consist essentially of anhydrous lactitol.

43. The lactitol product according to claim 29, wherein said particulate product additionally contains components such as excipients, active ingredients or other sweeteners.

44. A special sweetener which comprises microcrystalline lactitol according claim 29.

45. The special sweetener according to claim 44 which is mainly composed of said microcrystalline lactitol.

46. A bulk sweetener which comprises microcrystalline lactitol according to claim 29.

47. A diluent, carrier or excipient comprising microcrystalline lactitol according to claim 29.

48. A tablet produced by directly compressing a composition containing microcrystalline lactitol produced by contacting gas-suspended microcrystalline lactitol particles with a lactitol solution, drying said composition to cause lactitol microcrystallization, and conditioning said composition to provide a product comprising a multitude of microcrystals of lactitol agglomerated together in a random manner.

49. An edible, pharmaceutical or oral hygiene product which contains crystalline lactitol, characterized in that said product is selected from the confectionery, bakery products, cereals, desserts, jams, beverages, chocolate, chewing gum, ice cream, and dietetic products as well as in pharmaceutical products such as laxatives or oral hygiene products such as tooth paste and said lactitol is microcrystalline lactitol products by contacting gas-suspended microcrystalline lactitol particles with a lactitol solution, drying the resulting composition to cause lactitol microcrystallization, and conditioning said composition to provide a product comprising a multitude of microcrystals of lactitol agglomerated together in a random manner.

50. A directly compressible crystalline lactitol product for tabletting, characterized in that said lactitol product is produced by contacting gas-suspended microcrystalline lactitol particles with a lactitol solution, drying the resulting composition to cause lactitol microcrystallization, and conditioning said composition to provide a product comprising a multitude of microcrystals of lactitol agglomerated together in a random manner.

* * * * *